United States Patent [19]

Okano et al.

[11] 4,144,396

[45] Mar. 13, 1979

[54] PROCESS FOR PRODUCING ALKYLENE GLYCOL ESTERS

[75] Inventors: Takeshi Okano, Machida; Naoto Wada, Komae; Yoshimitsu Kobayashi, Tokyo, all of Japan

[73] Assignee: Mitsubishi Chemical Industries Limited, Tokyo, Japan

[21] Appl. No.: 810,626

[22] Filed: Jun. 27, 1977

[51] Int. Cl.$^2$ ............................................. C07C 67/05
[52] U.S. Cl. ................................. 560/246; 560/112; 252/438
[58] Field of Search ................ 560/243, 245, 246, 112

[56] References Cited

U.S. PATENT DOCUMENTS

| | | | |
|---|---|---|---|
| 3,349,118 | 10/1967 | Kohll | 560/243 |
| 3,444,189 | 5/1969 | Olivier | 560/243 |
| 3,542,857 | 11/1970 | Lutz | 560/246 |
| 3,686,287 | 8/1972 | Knights | 560/245 |
| 3,689,535 | 9/1972 | Kollar | 560/246 |
| 3,859,336 | 1/1975 | Aguilo | 560/243 |
| 3,872,164 | 3/1975 | Schmidt | 560/246 |
| 4,052,442 | 10/1977 | Tamura | 260/243 |

FOREIGN PATENT DOCUMENTS

| | | | |
|---|---|---|---|
| 44-20451 | 9/1969 | Japan | 560/243 |
| 45-14526 | 5/1970 | Japan | 560/243 |
| 45-14774 | 5/1970 | Japan | 560/243 |
| 45-19490 | 7/1970 | Japan | 560/243 |
| 45-32414 | 10/1970 | Japan | 560/243 |
| 45-32415 | 10/1970 | Japan | 560/243 |

OTHER PUBLICATIONS

Kunin, "Ion Exchange Resins," pp. 1-7, (1958).

*Primary Examiner*—James O. Thomas, Jr.
*Assistant Examiner*—Michael Shippen
*Attorney, Agent, or Firm*—Oblon, Fisher, Spivak, McClelland & Maier

[57] ABSTRACT

Alkylene glycol esters are produced by the reaction of an olefin, a carboxylic acid and molecular oxygen employing a bromine-containing substance and a nitrogen oxide as a catalyst.

10 Claims, No Drawings

PROCESS FOR PRODUCING ALKYLENE GLYCOL ESTERS

BACKGROUND OF THE INVENTION

1. Field of the Invention

This invention relates to a process for producing alkylene glycol esters, e.g., ethylene glycol esters, and more particularly, to the oxidative acylation of olefins.

2. Description of the Prior Art:

Alkylene glycol esters are useful as solvents and plasticizers. For example, ethylene glycol esters may be used as a solvent, or as an intermediate in the manufacture of ethylene glycol which is a commercially significant intermediate to polyethylene terephthalate. A variety of catalysts are known to be useful for the production of alkylene glycol esters by the reaction of olefins, carboxylic acids and molecular oxygen. U.S. Pat. No. 2,519,754 to Gresham et al., issued Aug. 22, 1950, discloses the use of hydrogen halides (preferably hydrobromic acid) or organic halides (preferably aliphatic bromides) as a catalyst. However, this process requires the use of high reaction temperatures in the range of 180° C. to 220° C. U.S. Pat. No. 2,497,408 to Gresham, issued Feb. 14, 1950, discloses a catalyst comprising tellurium dioxide, a halide ion and an oxygen compound of nitrogen such as nitrogen dioxide or nitrogen pentoxide which is used to reoxidize the tellurium to tellurium dioxide. Tellurium dioxide can be readily dissolved in a solution comprising hydrogen bromide and acetic acid. However, the addition of nitric acid results in the precipitation of orange crystals. U.S. Pat. No. 3,479,395 to J. L. Huguet et al., issued Nov. 18, 1969, discloses a catalyst comprising tellurium dioxide, an alkali metal bromide or alkaline earth metal bromide and a nitrogen oxide. U.S. Pat. No. 3,668,239 to Kollar, issued June 6, 1972, U.S. Pat. No. 3,689,535 to Kollar, issued Sept. 5, 1972, U.S. Pat. No. 3,778,468 to Kollar, issued Dec. 11, 1973 and U.S. Pat. No. 3,985,795 to Kollar, issued Oct. 12, 1976, disclose a catalyst comprising a variable valent metal cation, e.g. tellurium, selenium and a halogen source, e.g. a bromine-containing substance. This process, however, requires the use of high reaction temperatures above 150° C. A further disadvantage of this process is a decrease in the reaction rate with increasing a concentration of esters in the reaction solution. There is a need for a more efficient, selective and inexpensive process for the production of alkylene glycol esters from olefins and carboxylic acids.

SUMMARY OF THE INVENTION

Accordingly, it is an object of this invention to provide a commercially practical process for producing alkylene glycol esters in high yields and selectivities. Briefly, this and other objects of this invention, as will hereinafter become clear from the ensuing discussion, have been attained by reacting an olefin, a carboxylic acid and molecular oxygen employing a bromine-containing substance and a nitrogen oxide as a catalyst.

DESCRIPTION OF THE PREFERRED EMBODIMENTS

The method of this invention is illustrated by the following chemical equations:

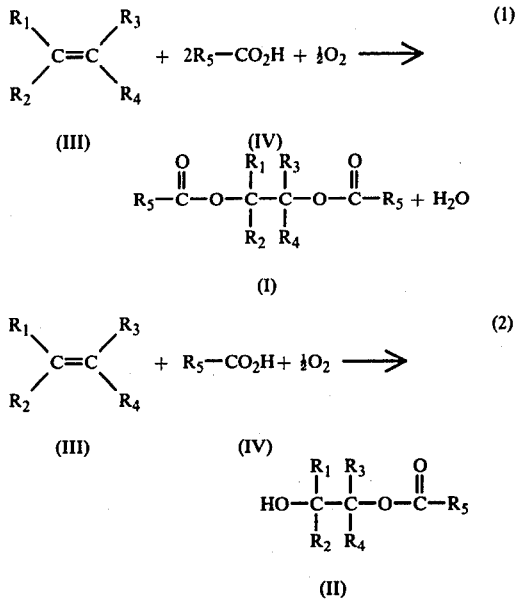

In the above formulas, $R_1$, $R_2$, $R_3$ and $R_4$ are selected from the group consisting of hydrogen, alkyl of 1-20 (preferably 1-10) carbon atoms and aryl of 1-20 (preferably 1-10) carbon atoms; and $R_5$ is alkyl of 1-20 (preferably 1-10) carbon atoms or aryl of 1-20 (preferably 1-10) carbon atoms. The above-described alkyl or aryl may be substituted with reaction-inert substituents such as halo, nitro, alkoxy, alkoxycarbonyl, carbonyl and the like.

Suitable olefins (III) for use in the present process include straight-chain olefins such as ethylene, propylene, 1-butene, 2-butene, 1-hexene, 1-octene, 1-decene and the like; and branched-olefins such as isobutylene, 2-methyl-1-pentene, 2-methyl-1-butene and the like. Preferred olefins are ethylene and propylene. Suitable carboxylic acids (IV) for use in the present process include aliphatic carboxylic acids such as acetic acid, monochloroacetic acid, propionic acid, butyric acid, valeric acid, isovaleric acid, octanoic acid, phenylacetic acid, phenylpropionic acid and the like; and aromatic carboxylic acids such as benzoic acid, toluic acid and the like. Preferred carboxylic acids are acetic acid, propionic acid and benzoic acid. Especially preferred is acetic acid. It is to be noted that when water is present in the reaction system in an amount sufficient to effect the hydrolysis of alkylene glycol diesters (I), alkylene glycol monoesters and alkylene glycols are obtained. It is also to be noted that the presence of water favors the formation of alkylene glycols by the oxidative hydroxylation of olefins as well as by the hydrolysis of the alkylene glycol esters. The characteristic feature of this invention is a new catalyst system comprising a bromine-containing substance and a nitrogen oxide. As used hereinabove, and as will be used hereinafter and in the claims, the term "a nitrogen oxide" is intended to include oxides of nitrogen such as NO, $NO_2$, $N_2O_3$, $N_2O_4$ and $N_2O_5$, nitrogen-containing oxyacids such as nitrous acid, hyponitrous acid and nitric acid, salts of the oxyacids, and esters of the oxyacids. It is believed that a bromine-containing substance acts as a catalyst while reversibly varying its oxidation number, and the bromine-containing substance is believed to be present in the reaction system in the form of $Br^-$, $Br_2$, $HBrO$, $HBrO_2$, $HBrO_3$, $BrO^-$, $BrO_2^-$, $BrO_3^-$, $R-CO_2Br$ (wherein R is alkyl),

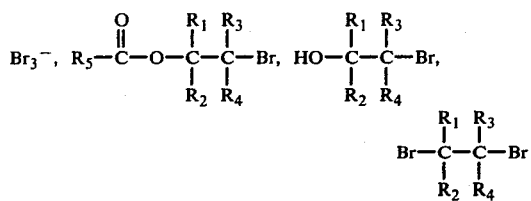

(wherein $R_1$, $R_2$, $R_3$, $R_4$ and $R_5$ are as defined herein above) or the like.

Any bromine-containing compound capable of affording in the reaction system a species of a bromine-containing substance which can reversibly vary its oxidation number may be introduced into the reaction system. Examples of such bromine-containing compounds are hydrobromic acid, hydrobromous acid, bromous acid, bromic acid and the salts thereof with metals such as alkali metals and alkaline earth metals, especially lithium, sodium, potassium, magnesium, and with copper; complex compounds of bromine; bromine; and organic bromine compounds, such as ethyl bromide, 1,2-dibromoethane, isopropyl bromide, 2-bromoethyl acetate, ethylene bromohydrin and the like which readily liberate bromide ion by solvolysis under reaction conditions. The amount of the bromine-containing substance to be used is not critical, and is normally up to one gram equivalent per liter of the reaction solution. It is also believed that a nitrogen oxide which is another essential component of the catalyst system of this invention acts as a catalyst, in a manner similar to that of the bromine-containing substance, while reversibly varying its oxidation number, and the nitrogen oxide is believed to be present in the reaction system in the form of NO, $NO_2$, $N_2O_3$, $N_2O_4$, $N_2O_5$, $HNO_3$, $NO_2^-$, $NO_3^-$, alkyl nitrites (R—ONO wherein R is alkyl), alkyl carbonyl nitrites (

wherein R is alkyl) or the like. Therefore, any nitrogen oxide capable of affording in the reaction system a species of a nitrogen oxide which can reversibly vary its oxidation number may be introduced into the reaction system. Examples of such nitrogen oxides are nitric acid and the salts thereof such as alkali metal, alkaline earth metal and copper nitrates, and the like; nitrous acid and the salts thereof such as alkali metal, alkaline earth metal and copper nitrites; nitrogen oxides such as NO, $NO_2$, $N_2O_3$, $N2O4$, $N2O5$ and the like; alkyl esters of nitrous acid; alkyl esters of nitric acid; and a mixture thereof.

Suitable nitrogen oxides are nitric acid; alkali metal salts of nitric acid such as lithium nitrate, sodium nitrate and potassium nitrate; alkaline earth metal salts of nitric acid such as magnesium nitrate; aluminum nitrate; NO; $NO_2$; $N_2O_3$; $N_2O_5$; nitrous acid; alkali metal salts of nitrous acid such as lithium nitrite and sodium nitrite; alkaline earth metal salts of nitrous acid such as magnesium nitrite; aluminum nitrite; alkyl esters of nitrous acid having 1-10 carbon atoms such as ethyl nitrite; and alkyl esters of nitric acid having 1-10 carbon atoms such as ethyl nitrate, ethylene dinitrate. The preferred nitrogen oxides are nitric acid, alkali metal salts of nitric acid and $NO_2$. Especially preferred are nitric acid, lithium nitrate and $NO_2$.

The amount of the nitrogen oxide to be used is not critical, and is generally up to one mole per liter of the reaction solution.

The reaction mechanism for the process of this invention whereby alkylene glycol esters are obtained by the oxidative acylation of olefins is not fully understood. However, the following mechanism is possible.

Oxidation of a nitrogen oxide with an oxidizing agent, e.g., molecular oxygen converts the nitrogen oxide to its oxidized form which then oxidizes a reduced form of a bromine-containing substance, e.g., bromice ion, being present in the system, to give its oxidized form, e.g., $Br_2$, $Br_2O$, whereby the nitrogen oxide becomes reduced to its initial valence state. The oxidized form of the bromine-containing substance being formed, alone, or with the aid of a carboxylic acid or the like, oxidizes an olefin to give alkylene glycol esters, bromoalkyl esters of carboxylic acids such as 2-bromoethyl acetate and the like, and alkyl bromide such as dibromoethane and the like, and alkylene bromohydrins such as ethylene bromohydrin and the like. The bromine-containing substance in a higher state of oxidation, when used in the direct production of alkylene glycol esters, becomes reduced to its initial valence state. Bromine directly captured by a hydrocarbon, e.g., bromine in an alkyl bromide such as dibromoethane is displaced by a carboxylic acid thereby giving bromice ion and an alkylene glycol ester. This substitution is carried out by a solvolysis under reaction conditions.

While repeating the above-described reaction as one cycle, the chain reaction proceeds.

It can be said that alkyl bromides such as dibromoethane, alkylene bromohydrins such as ethylene bromohydrin, and bromoalkyl esters of carboxylic acids such as 2-bromoethyl acetate which are formed during the course of the reaction are intermediates in the formation of the desired alkylene glycol esters. They can be recovered and returned to the reactor. Alternatively, they can be converted to alkylene glycol esters by a solvolysis.

It follows from the above that the only requirement for the nitrogen oxide and the bromine-containing substance used in the process of this invention is that they be capable of undergoing alternative oxidation and reduction under the reaction conditions.

Therefore, any nitrogen oxide and bromine-containing substance each capable of undergoing alternative oxidation and reduction in the reaction system can be used regardless of their initial valence state.

As stated above, the oxidizing agent employed in the process of this invention oxidizes the nitrogen oxide from a lower valence state to a higher valence state. In general, molecular oxygen is used as an oxidizing agent.

However, it goes without saying that, in place of molecular oxygen, an oxidizing agent capable of oxidizing nitrogen oxides, such as hydrogen peroxide, organic peroxides, persulfates, chlorine, ozone or the like can be used.

In order for the process of this invention to be economically advantageous, it is preferred to use molecular oxygen as an oxidizing agent. Oxygen may be introduced into the reaction mixture as a stream of the substantially pure gas. Alternatively, it may be introduced as air or as a mixture of oxygen with an inert gas such as nitrogen.

In general, the reaction is carried out in the presence of a solvent. Examples of such solvents are the olefin starting materials, the carboxylic acid starting materials, the alkylene glycol ester products, glycols and a mixture thereof. Preferably, the carboxylic acid is used as a solvent as well as the source of the acid moiety of the desired ester.

In a continuous process, it is preferred that the glycol and its ester be separated from the reaction solution, whereas the unreacted carboxylic acid and olefin be recovered for reuse.

If desired, organic or inorganic solvents which are substantially inert to the reaction may be used as a solvent or a portion of the solvent. For example, when the reaction is carried out employing ethylene as an olefin, acetic acid as a carboxylic acid and the same amount of water as that of acetic acid as a solvent, the reaction rate and the selectivity are nearly equal to those obtained when water is not added, and the main products are ethylene glycol monoacetate and ethylene glycol diacetate.

When water is added in an amount larger than that of acetic acid, ethylene glycol is formed as a by-product. Although, the formation of glycols is not a hindrance to commercial development of the process of this invention, it is preferred that the water content in the reaction solution be not more than 15 weight percent in order for ethylene glycol diacetate to be a main product.

The process of this invention can be carried out by introducing into the reactor in addition to the above-described catalyst system a promoter. Suitable promotors are carriers such as activated carbon, alumina, silica, silica-alumina, an inorganic ion exchanger (sodium or potassium alumino-silicate) and the like. These promotors are known as an absorbent for low molecular weight substances.

The role of the promotor is not fully understood.

However, it is believed that the promotor facilitates alternative oxidation and reduction in the reaction system by repeated adsorption and desorption of unsaturated hydrocarbons, oxygen, nitrogen oxides or bromine-containing substances on the promotor. The promotor can be used as a fixed bed or fluidized system such as a slurry dispersion. The reaction temperature is not critical in the present invention except to retain a liquid phase. The lower the temperature, the lower is the reaction rate. On the other hand, the higher the temperature, the lower is the solubility of the gaseous starting materials (olefins, oxygen, bromine-containing substances and nitrogen oxides) in the reaction mixture. Accordingly, the reaction temperature is in the range of from 80° to 60° C., and preferably from 120° to 150° C.

The reaction pressure is not an important variable and any pressure sufficient to maintain a liquid phase at the temperature being used is satisfactory. The reaction rate becomes higher as the reaction pressure increases. However, the high reaction pressure requires the use of a costly high pressure reactor. Accordingly, the preferred reaction pressure is generally in the range of from atmospheric pressure to about 100 Kg/cm$^2$.

The reaction is carried out in any suitable apparatus, e.g., fixed bed, slurry-type and moving bed reactor, and can be done batchwise or continuously.

In general, the carboxylic acid is added in liquid form. In a continuous process, the unreacted carboxylic acid, after leaving the reactor, is separated from the reaction mixture for reuse.

The gaseous olefin is introduced alone or in combination with molecular oxygen into the reactor. The liquid or solid olefin is introduced into the reactor alone or as a solution by dissolving it in a reaction medium, or as a gas by gasifying it in a vaporizor. The unreacted olefin, after leaving the reactor, is separated from the reaction products for reuse.

The bromine-containing substance and the nitrogen oxide are separated from the reaction products, and can be reused after being subjected to a suitable operation for regeneration, e.g., reoxidation, if necessary.

Some of the advantages resulting from the use of the catalyst of this invention for producing alkylene glycol esters include the following:

(1) The extent to which increasing a concentration of the alkylene glycol esters in the reaction solution decreases the reaction rate is lower as compared with the prior art processes.

(2) The use of a suitable catalyst, e.g. HBr-HNO$_3$, makes homogeneous liquid phase reaction possible.

(3) The addition of metals as a catalyst has no beneficial effect and is not needed for the successful production of the alkylene glycol esters.

Having generally described this invention, a more complete understanding can be obtained by reference to certain examples and reference examples which are provided herein for purposes of illustration only and are not intended to be limiting in any manner.

In the following examples and reference examples, the products, the conversion and the selectivity were investigated by gas chromatographic analysis.

EXAMPLE 1

To a 100 ml round bottom flask fitted with an agitator, a reflux condenser, a gas inlet tube and a thermometer were added 2.38 g (20 millimoles) of potassium bromide, 0.69 g (10 millimoles) of lithium nitrate, 0.5 g of activated carbon prepared from coconut shells (manufactured by Dai-ichi Carbon Industries Company) and 80 ml of acetic acid. The flask was set up in a bath maintained at 80° C. A gas mixture comprising oxygen, nitrogen and ethylene was fed in the proportions by volume of 0.8 O$_2$/7.2 N$_2$/1.2 ethylene through the reaction mixture at a rate of 1.15 standard liters per hour with continuous stirring of the reaction mixture.

At the conclusion of the one hour reaction period, the yields of ethylene glycol diacetate (hereinafter referred to as "EGDA"), 2-bromoethyl acetate (hereinafter referred to as "2-BA") and 1,2-dibromoethane (hereinafter referred to as "1,2-DE") are 2 millimoles each. The combined yields of EGDA, 2-BA and 1,2-DE based on the reacted ethylene were more than 99%.

EXAMPLE 2

A 100 ml titanium-lined autoclave was charged with 30 ml of acetic acid, 1.20 ml (11 millimoles calculated as HBr) of 48% hydrobromic acid and 0.14 g (2 millimoles) of lithium nitrate, and then pressurized with 3 kg/cm$^2$ (absolute pressure) of ethylene and 30 kg/cm$^2$ (absolute pressure) of a gas mixture comprising by volume 96% of nitrogen and 4% of oxygen. The reactor was heated to 150° C. with stirring and the reaction was carried out at this temperature for 2 hours.

The yields of EGDA, 2-BA and 1,2-DE are 2 millimoles, 1 millimole and 3 millimoles, respectively.

Analysis indicated the absence of other products starting from ethylene.

EXAMPLE 3

A 3 ml glass ampule was charged with 1 ml of a mixture prepared by mixing 4.34 g (23.1 millimoles) of 1,2-DE, 18.9 g (315 millimoles) of acetic acid, 5 g (278 millimoles) of water and 1.48 g (8.8 millimoles calculated as HBr) of 48% hydrobromic acid. The ampule was vented and sealed by means of a vacuum system, and then set up in an oil bath maintained at 160° C.

At the end of the two hour reaction period, the ampule was cooled rapidly and then opened. The conversion of 1,2-DE was 55.0%. The selectivities of 1,2-DE to 2-BA and EGDA were 60% and 40%, respectively. A trace amount of ethylene glycol monoacetate (hereinafter referred to as "EGMA") was detected.

EXAMPLE 4

A 5 ml glass ampule was charged with 2 ml of a mixture prepared by mixing 2.80 g (16.8 millimoles) of 2-BA, 18 ml (315 millimoles) of acetic acid and 5 g (278 millimoles) of water. The ampule was vented and sealed by means of a vacuum system, and then set up in an oil bath maintained at 160° C.

At the end of the two hour reaction period, the ampule was cooled rapidly and then opened. The conversion of 2-BA was 75%. The selectivities of 2-BA to EGDA, 1,2-DE and EGMA were 60%, 30% and 10%, respectively. A trace amount of ethylene bromohydrin was detected.

EXAMPLE 5

A 300 ml titanium-lined autoclave, fitted with a stirring apparatus, a gas inlet tube, a liquid inlet tube, a gas exit tube through a reflux condenser, and a liquid exit tube, was charged with 6.88 g of 48% hydrobromic acid, 3.0 g of 60% nitric acid and 90.12 g of acetic acid. The autoclave was pressurized to a pressure of 30 kg/cm$^2$ gauge with a gas mixture comprising by volume 85.1% of nitrogen, 5.0% of oxygen and 9.9% of ethylene, and then heated gradually to 130° C. while maintaining the pressure at 30 kg/cm$^2$ gauge and feeding the gas mixture into the reactor at such a rate that a flow rate of the gas at the exit from the reactor is 15 standard liters per hour. A mixture of 48% hydrobromic acid, 60% nitric acid and acetic acid having the same composition as that initially added to the autoclave was pumped into the reactor at a rate of 20 ml per hour under the above conditions, while the reaction mixture was withdrawn from the reactor via the liquid exit pipe at a rate of 20 ml per hour. After steady-state was reached, the reaction was carried out continuously for 8 hours under the above conditions.

The amounts of the reacted ethylene and oxygen were 0.22 and 0.12 mole/hr·kg of reaction solution, respectively. The amount of the formed carbon dioxide was 1.65% of the reacted ethylene. $N_2O$, NO and $NO_2$ were detected in the waste gas.

The compounds other than acetic acid in the reaction solution had the following composition:
EGDA; 57.9 weight percent
EGMA; 38.7 weight percent
ethylene bromohydrin; 1.6 weight percent
The combined yields of EGDA, EGMA and ethylene bromohydrin based on the reacted ethylene were 96.5%.

EXAMPLE 6

Example 5 was repeated except that the reaction temperature was 160° C.

The amounts of the reacted ethylene and oxygen were 0.21 and 0.18 mole/hr·kg of reaction solution. The amount of the formed carbon dioxide was 5.93% of the reacted ethylene.

EXAMPLE 7

The autoclave, as described in Example 5, was charged with 13.5 g of 48% hydrobromic acid, 3 g of 60% nitric acid, 40 g of EGDA and 43.5 g of acetic acid. The reaction was carried out in the same manner as in Example 5 with the exception that a mixture of 48% hydrobromic acid, 60% nitric acid, EGDA and acetic acid having the same composition as that initially added to the autoclave in this Example was pumped. After steady-state was reached, the amounts of the reacted ethylene and oxygen were 0.3 and 0.15 mole/hr·kg of reaction solution, respectively. The amount of the formed carbon dioxide was 1.67% of the reacted ethylene. Trace amounts of $N_2O$, NO and $NO_2$ were detected.

The compounds other than acetic acid in the reaction solution had the following composition:
EGDA; 59.7 weight percent
EGMA; 32.7 weight percent
Ethylene bromohydrin; 2.7 weight percent
2-BA; 1.4 weight percent
Ethylene glycol; 1.5 weight percent

REFERENCE EXAMPLE 1

The autoclave, as described in Example 5, was charged with 13.5 g of 48% hydrobromic acid, 40 g of EGDA and 46.5 g of acetic acid. The reaction was carried out in the same manner as in Example 5 with the exception that a mixture of 48% hydrobromic acid, EGDA and acetic acid having the same composition as that initially added to the autoclave in this Example was pumped.

After steady-state was reached, the amounts of the reacted ethylene and oxygen were 0.04 and 0.02 mole/hr·kg of reaction solution, respectively.

The compounds other than acetic acid in the reaction solution had the following composition:
EGDA; 94.5 weight percent
EGMA; 3.7 weight percent
2-BA; 1.8 weight percent

Having now fully described the invention, it will be apparent to one of ordinary skill in the art that many changes and modifications can be made thereto without departing from the spirit or scope of the invention as set forth herein.

What is claimed as new and intended to be covered by Letters Patent of the United States:

1. In a process for the production of alkylene glycol esters having the formula (I):

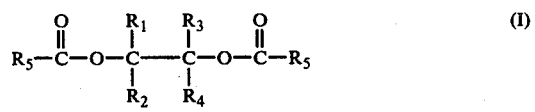

wherein $R_1$, $R_2$, $R_3$, and $R_4$ are selected from the group consisting of hydrogen, $C_1$–$C_{20}$ alkyl and $C_1$–$C_{20}$ aryl;

and $R_5$ is $C_1$–$C_{20}$ alkyl or $C_1$–$C_{20}$ aryl, and/or the formula (II):

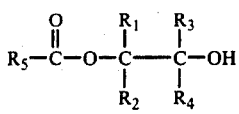

wherein $R_1$, $R_2$, $R_3$, $R_4$ and $R_5$ are as defined herein above, which comprises reacting an olefin having the formula (III):

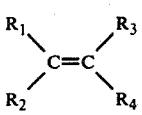

wherein $R_1$, $R_2$, $R_3$, and $R_4$ are as defined herein above, a carboxylic acid having the formula (IV):

$$R_5\text{—}CO_2H \qquad (IV)$$

wherein $R_5$ is as defined herein above, and molecular oxygen, the improvement consisting essentially of: reacting said olefin and said carboxylic acid in the presence of a catalyst consisting essentially of a bromine-containing compound selected from the group consisting of hydrobromic acid, hypobromous acid, bromous acid, bromic acid, alkali metal, alkaline earth metal and copper salts of said acids, organic bromine compounds which liberate bromide ion upon solvolysis and bromine, and a nitrogen oxide selected from the group consisting of $NO, NO_2, N_2O_3, N_2O_4, N_2O_5$, nitric acid, nitrous acid and alkali metal, alkaline earth metal, aluminum and copper salts of said acids, alkyl nitrites, alkylcarbonyl nitrites and alkyl nitrates.

2. The process of claim 1 wherein $R_1$, $R_2$, $R_3$ and $R_4$ are selected from the group consisting of hydrogen, $C_1$–$C_{10}$ alkyl and $C_1$–$C_{10}$ aryl; and $R_5$ is $C_1$–$C_{10}$ alkyl or $C_1$–$C_{10}$ aryl.

3. The process of claim 2 wherein the olefin is ethylene or propylene, and the carboxylic acid is acetic acid.

4. The process of claim 1 wherein the reaction i carried out in the liquid phase.

5. The process of claim 1 wherein the nitrogen oxide is selected from the group consisting of nitric acid, alkali metal salts of nitric acid, alkaline earth metal salts of nitric acid, aluminum nitrate, nitrous acid, alkali metal salts of nitrous acid, alkaline earth metal salts of nitrous acid, aluminum nitrite, alkyl esters of nitrous acid having 1–10 carbon atoms and alkyl esters of nitric acid having 1–10 carbon atoms.

6. The process of claim 5 wherein the nitrogen oxide is nitric acid, an alkali metal salt of nitric acid or $NO_2$.

7. The process of claim 1 wherein the amount of the nitrogen oxide to be used is up to one mole per liter of the reaction solution.

8. The process of claim 1, wherein the amount of the bromine-containing substance present is an amount of up to one gram equivalent per liter of the reaction solution.

9. In the process for the production of alkylene glycol esters having the formula (I):

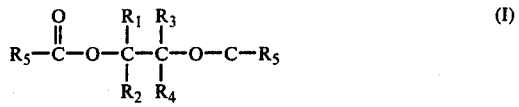

wherein $R_1$, $R_2$, $R_3$ and $R_4$ are selected from the group consisting of hydrogen, $C_1$–$C_{20}$ alkyl and $C_1$–$C_{20}$ aryl; and $R_5$ is $C_1$–$C_{20}$ alkyl or $C_1$–$C_{20}$ aryl, and/or the formula (II):

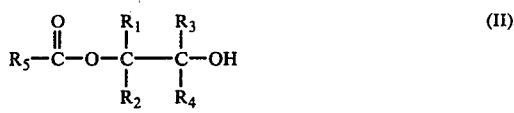

wherein $R_1$, $R_2$, $R_3$, $R_4$ and $R_5$ are as defined herein above, which comprises reacting an olefin having the formula (III):

wherein $R_1$, $R_2$, $R_3$ and $R_4$ are as defined herein above, a carboxylic acid having the formula (IV):

$$R_5\text{—}CO_2H \qquad (IV)$$

wherein $R_5$ is as defined herein above, and molecular oxygen, the improvement consisting essentially of: reacting said olefin and said carboxylic acid in the presence of a catalyst consisting essentially of a bromine-containing compound selected from the group consisting of hydrobromic acid, hypobromous acid, bromous acid, bromic acid, alkali metal, alkaline earth metal and copper salts thereof, organic bromine compounds which liberate bromide ion upon solvolysis and bromine, and a nitrogen oxide selected from the group consisting of $NO, NO_2, N_2O_3, N_2O_4, N_2O_5$, nitric acid, nitrous acid and alkali metal, alkaline earth metal, aluminum and copper salts of said acids, alkyl nitrites, alkylcarbonyl nitrites and alkyl nitrates, and a promotor component selected from the group consisting of activated carbon, alumina, silica, silica-alumina and an inorganic ion exchanger.

10. The process of claim 9 wherein the reaction temperature is in the range of 120° to 150° C.

* * * * *